United States Patent
Purvis (10) Patent No.: US 8,163,163 B2
(45) Date of Patent: Apr. 24, 2012

(54) METHOD OF ELECTROCHEMICAL ANALYSIS OF AN ANALYTE

(75) Inventor: Duncan Ross Purvis, Cambridge (GB)

(73) Assignee: Sensortec Limited, St. Helier (GB)

( * ) Notice: Subject to any disclaimer, the term of this patent is extended or adjusted under 35 U.S.C. 154(b) by 538 days.

(21) Appl. No.: 11/718,746

(22) PCT Filed: Nov. 10, 2005

(86) PCT No.: PCT/GB2005/004357
§ 371 (c)(1),
(2), (4) Date: May 7, 2007

(87) PCT Pub. No.: WO2006/051310
PCT Pub. Date: May 18, 2006

(65) Prior Publication Data
US 2008/0164154 A1 Jul. 10, 2008

(30) Foreign Application Priority Data
Nov. 11, 2004 (GB) .................................. 0424960.3

(51) Int. Cl.
*G01N 27/327* (2006.01)
*G01N 27/416* (2006.01)

(52) U.S. Cl. ................. 205/792; 204/229.8; 204/403.11; 204/403.1; 205/777.5

(58) Field of Classification Search .................... 205/81, 205/777.5, 779, 792; 204/229.8, 403.11, 204/403.1
See application file for complete search history.

(56) References Cited

U.S. PATENT DOCUMENTS

| | | | | |
|---|---|---|---|---|
| 5,431,789 A | * | 7/1995 | Huber et al. | 205/780.5 |
| 6,251,260 B1 | | 6/2001 | Heller et al. | |
| 2002/0175075 A1 | * | 11/2002 | Deng et al. | 204/403.01 |
| 2004/0157337 A1 | * | 8/2004 | Burke et al. | 436/70 |

FOREIGN PATENT DOCUMENTS

| | | |
|---|---|---|
| DE | 41 00 727 A1 | 7/1992 |
| WO | WO 92/19959 | 11/1992 |
| WO | WO 96/02001 A | 2/1996 |
| WO | WO 00/11473 | 3/2000 |
| WO | WO 03019171 A1 * | 3/2003 |

OTHER PUBLICATIONS

Cai, H et al., Biosensors & Bioelectronics, 18(11):1311-1319 (2003).

* cited by examiner

*Primary Examiner* — Kaj K Olsen
*Assistant Examiner* — Susan Thai
(74) *Attorney, Agent, or Firm* — Antoinette G. Giugliano, PC (57) ABSTRACT

A method of electrochemical analysis using a sensor electrode specific for an analyte under test. The method comprises immersing the sensor electrode in a sample solution suspected of containing the analyte; forming an electrochemically active complex by exposure to solutions containing secondary receptors or competing molecules labelled with a charged or enzyme label; and subsequently exposing the sensor to an electrochemically active solution. The measurement step comprises driving the sensor electrode potential to a predetermined fixed potential by applying a current or activation waveform then monitoring the potential difference between the sensor electrode and a reference electrode following removal of the holding current. Current, rate and potential can all be measured and used to determine analyte concentration or sensor state.

19 Claims, 4 Drawing Sheets

METHOD OF ELECTROCHEMICAL ANALYSIS OF AN ANALYTE

RELATED APPLICATIONS

This application is the U.S. National Phase of International Application No. PCT/GB2005/004357, filed Nov. 10, 2005, published in English, which application claims priority under 35 U.S.C. §119 or 365 to Great Britain Application No. 0424960.3, filed Nov. 11, 2004. The entire teachings of the above applications are incorporated herein by reference.

FIELD OF THE INVENTION

This invention relates to an improved method for electrochemical detection of analytes.

BACKGROUND TO THE INVENTION

WO 00/011473 describes methods of electrochemical analysis of an analyte (e.g antigen) in complex samples by using potentiometric sensor electrodes for electrochemical detection of the analyte. The sensor electrodes for use in these methods generally comprises an electrically conductive electrode coated with an electroconductive polymer (e.g. polypyrrole). Receptor molecules capable of selectively binding to the analyte to be detected are immobilised in or adsorbed to the electroconductive polymer to enable the detection of the desired analyte. Detection is achieved via formation of a specific complex, containing the analyte and also a label component which facilitates electrochemical detection, bound to the receptor molecule at the surface of the sensor electrode.

The detection methods of WO 00/011473 generally comprise a number of steps summarised as follows:
(a) providing a sensor electrode having an electroconductive polymer coating an having immobilised or adsorbed receptors specific for the analyte of interest;
(b) treating the sensor electrode by immersion in a sample so that said desired analyte binds to the immobilised or adsorbed receptors at the sensor surface to form a complex which also includes a label component;
(c) removing the sensor electrode from the sample and subsequently monitoring the electric potential difference between the treated sensor electrode and a reference electrode when both are immersed in a suitable inactive measuring buffer, and subsequently;
(d) monitoring the electric potential difference between the sensor electrode and a reference electrode following exposure to another buffer, but one that is electrochemically active, thus promoting electrochemical activity of the label component.

WO 03/019171 describes improved methods for the production of potentiometric sensor electrodes and also improved methods of electrochemical detection using these sensor electrodes. However, the improved methods of electrochemical detection described in WO 03/019171 still rely on a first measurement of electric potential difference between the treated sensor electrode and a reference electrode when both are immersed in a suitable inactive measuring buffer, and subsequent monitoring of the electric potential difference between the sensor electrode and a reference electrode following exposure to another buffer which promotes electrochemical activity of the label component.

The present inventors have how developed a simplified method of electrochemical detection which does not require a separate step of measuring the electric potential difference between the treated sensor electrode and a reference electrode when both are immersed in an inactive measuring buffer, prior to exposure to a buffer which promotes electrochemical activity of the label component, to be carried out each time the method is used for detection of a given analyte.

SUMMARY OF THE INVENTION

In accordance with the invention there is provided a method of electrochemical detection of an analyte in a sample comprising:
(a) providing a sensor electrode comprising an electrically conductive electrode coated with a layer of electroconductive polymer;
(b) contacting the sensor electrode with a solution comprising the sample to be tested for the presence of the analyte under conditions which permit formation of an electrochemically active analyte complex comprising the analyte and an electrochemically active label component on the electroconductive polymer layer;
(c) contacting the sensor electrode plus electrochemically active analyte complex with an electrochemically active measuring solution which promotes electrochemical activity of the electrochemically active analyte complex;
(d) applying a current to induce a pre-determined holding potential on the sensor electrode,
(e) removing the current and allowing the sensor electrode to return to an open circuit resting potential;
(f) measuring one or more of the following parameters as an indicator of the amount of analyte present in the sample:
 (i) the difference between the holding potential and the open circuit resting potential,
 (ii) the rate at which the sensor electrode returns from the holding potential to the open circuit resting potential,
 (iii) the amount of current required to hold the sensor electrode at the pre-determined holding potential.

The method of the invention is a simplification of the methods described in, for example, and WO 00/11473 and WO 03/019171, since there is no requirement for separate steps of measuring electric potential difference between the sensor electrode and a reference electrode in an inactive measuring buffer and in a second buffer which promotes electrochemical activity of the label component. Thus, there is no need to prepare a separate inactive measuring solution and no need for additional fluid and/or electrode manipulation steps to transfer the sensor electrode from the inactive measuring solution to an active measuring solution.

DETAILED DESCRIPTION OF THE INVENTION

The method of the invention utilises sensor electrodes coated with a layer of electroconductive polymer. The basic characteristics of these sensor electrodes, and also preferred methods for production of the electrodes by coating of electrically conductive electrodes with a layer of conductive polymer, are described more fully below and also in the applicant's published International Patent Applications WO 00/11473 and WO 03/019171, the contents of which are incorporated herein in their entirety by reference.

The sensor electrodes may be essentially any suitable electrodes comprising a conductive or semi-conductive layer. Suitable electrodes include standard potentiometric electrodes possessing metallic or quasi-metallic conductivity that are stable in aqueous media, e.g. gold and other noble metal electrodes. The sensor electrodes are electrochemically coated, preferably on at least a portion of at least one major surface, with a layer of electroconductive polymer, e.g. polypyrrole, polythiophene, polyfuran, polyaniline, etc. A thin layer of the polymer is deposited onto the electrically conductive electrode by electrochemical synthesis from a solution comprising monomers, a polar solvent and a background electrolyte, according to procedures, which are known in the art (see WO 00/11473 and WO 98/37409). Pyrrole is the preferred monomer, but other monomers such as thiophene, furan or aniline may also be used. Combinations of two or more of these monomers may also be used, leading to the production of conductive co-polymers.

The preferred supporting electrolyte is sodium dodecylsulphate but other electrolytes may be used. The electrolyte also serves as a doping agent. Deionised water is preferably used as the polar solvent.

The electrochemical polymerisation solution generally consists of an aqueous solution of monomers and supporting electrolyte. However, other components may be added to the polymerisation solution such as, for example, components that provide specific functional groups that can be used as linkers for biological receptors or for chemical modification of the sensor surface (see WO 00/11473 and WO 98/37409).

Electrochemical polymerisation is typically carried out in a three electrode cell comprising of sensor electrode(s) to be coated, the auxiliary electrode and the reference electrode. Suitable assemblies have been described in the prior art (see WO 00/11473 and references contained therein). Multiple sensor electrodes can be combined in a block with one electrical contact. An entire array of sensing electrodes may be coated in a single polymerisation reaction. This may use either a single auxiliary electrode or one auxiliary electrode per pair of sensing and reference electrodes. For example, arrays that include a third counter-electrode associated with each pair of sensing and reference electrodes (e.g. for amperometric analysis) may be coated using the third counter-electrode as the auxiliary electrode. In a further arrangement, the reference electrodes may be used as the auxiliary (counter) electrode for the polymerisation step. The reference electrode may be manipulated to function as an auxiliary electrode for polymerisation, for example with Ag/AgCl electrodes the ratio of Ag/AgCl may be temporarily altered such that it functions as an auxiliary electrode for polymerisation, and then restored to function as a reference electrode after polymerisation.

As is well known to persons skilled in the art, electroconductive polymers are often doped at the electrochemical synthesis stage in order to modify the structure and/or conduction properties of the polymer. The ease with which ion exchange takes place and the rapidity with which ion equilibrium is attained for electroconductive polymers immersed in a solution are essentially dependent on the size of the dopant anion introduced at the electrodeposition stage: the larger the ionic radius of the dopant anion, the more readily ion exchange reactions take place and the more rapidly a state of equilibrium is reached. This is directly linked to the value and rate of change of the potential of the "metal electrode electroconductive polymer" system in response to variation in the ion composition of the solution. The type of the response (anionic, cationic, redox) and its rate can be determined during the polymerisation.

A typical dopant anion is sulphate ($SO_4^{2-}$), which is incorporated during the polymerisation process, neutralising the positive charge on the polymer backbone. Sulphate is not readily released by ion exchange and thus helps to maintain the structure of the polymer.

For redox and pH sensitive sensors it is preferred to use a salt whose anions have a large ionic radius as the background electrolyte when preparing the electrochemical polymerisation solution. In this case ion response is minimised and redox or pH response predominate, potentiometric response is provided by electron exchange between the polymer film and surrounding solution.

Suitable salts whose anions have large ionic radius include sodium dodecyl sulphate and dextran sulphate. The concentration of these salts in the electrochemical polymerisation solution is varied according to the type of test within the range of from 0.0001 to 0.05 M.

Redox response can be increased by incorporating into the polymer dopant ions, which can change their redox state due to the changes in the surrounding solution giving the sensor the additional change in redox state. The dopant should be in reduced form if one of the solution components is oxidized and vice versa. $K_3[Fe(CN)_6]/K_4[Fe(CN)_6]$ can be given as an example for both cases. The concentration of these electrolytes in the electrochemical polymerisation solution can be varied within the range of from 0.001 to 0.1 M to meet specific requirements of the test.

The surfaces of electroconductive polymer-coated electrodes can be further modified by coating with biological molecules for specific binding of the analyte (also referred to herein as "receptors") or other functional groups or molecules which can be used as linkers or adaptors for biological molecules or for chemical modification of the sensor surface (see WO 00/11473, WO 98/37409 and WO 96/02001).

Biological molecules, for example receptor molecules capable of specifically binding to the analyte under test, can be immobilised onto a sensor using well known techniques for solid phase coating. Biological molecules may be incorporated into the electroconductive polymer during the polymerisation reaction, or they may be adsorbed onto the surface of the coated sensing electrode in a separate modification step after the polymer coating step, or they may be covalently linked to the polymer coating (see WO 00/11473, WO 98/37409 and WO 96/02001).

In a particular embodiment the biological molecules may be "adaptor molecules" which enable the attachment of further molecules, or even whole cells, to the surface of the sensor via a specific binding interaction. With the selection of appropriate adaptor molecules it is also possible to manufacture "universal" sensing electrodes containing adaptor molecules capable of binding to a whole range of different receptor molecules. Specificity for the analyte under test is conferred on the "universal" sensing electrode simply by binding to the adaptor molecules receptors of the appropriate specificity.

The proteins avidin and streptavidin are preferred for use as adaptor molecules. Investigations carried out by the authors of the present invention have shown that avidin and streptavidin immobilised in an electroconductive polymer film, retain their native properties for an extended period of time (at least one year and possibly longer) and can be used throughout this period to link with biotin conjugated receptors. Techniques that allow the conjugation of biotin to a wide range of different molecules are well known in the art. Thus sensing electrodes with immobilised avidin or streptavidin can easily made specific for a given analyte merely by binding of the appropriate biotinylated receptors via biotin/avidin or biotin/streptavidin binding interactions.

Although avidin and streptavidin are the preferred adaptor molecules it is within the scope of the invention to use alternative adaptor molecules, for example protein A, protein G, lectins and FITC. The incorporation of adaptor molecules enables other biological molecules or whole cells to be attached to the surface of the sensing electrode, for example via protein A/antibody, protein G/antibody, FITC/anti FITC or lectin/sugar binding interactions. Biological molecules may alternatively be absorbed directly or covalently bound to the polymer-coated sensor surface.

In order to perform the method of the invention the sensor electrode is first brought into contact with a solution comprising the sample to be tested for the presence of the analyte. As used herein the term "sample" includes within its scope any material which it is desired to test for the presence of analyte, including but not limited to biological fluids such as whole blood, serum, plasma, urine, lymph, cerebrospinal fluid, ascites, pleural effusion or semen, environmental fluids such as effluents or waste-products of the chemical industry, materials used or produced in the food and drink industry, for example milk, or a dilution or extract of any of the above. The sample may also comprise a solution or extract of a solid material. It will be appreciated that certain types of samples may be tested directly without the need for any further treatment, such as dilution. Such samples are also to be considered as "solutions comprising the sample to be tested for the presence of the analyte". The solution comprising the sample to be tested for the presence of the analyte may also be referred to herein as a "test solution".

Contact between the sensor electrode and the solution comprising the sample to be tested for the presence of the analyte can be achieved by fully or partially immersing the sensor electrode in the solution. In this embodiment the solution may be conveniently placed in a suitable container, such as for example the well of a microtiter plate, a micro-centrifuge tube or any other vessel of suitable size to accommodate the sensor electrode or an electrode assembly comprising the sensor electrode. Alternatively, contact may be achieved by placing a drop of the solution onto the surface of the sensor electrode. The volume of test solution will generally be from 5 to 200 µl depending on the geometric dimensions of the sensing electrode.

The sensor electrode is contacted with the solution comprising the sample for sufficient time and under conditions which permit formation of a specific electrochemically active analyte complex at the surface of the sensor electrode, and more specifically on the electroconductive polymer layer of the sensor electrode. The contact time between the sensor electrode and test solution is, by way of illustration not limiting to the invention, typically from 3 to 30 minutes at 15-40° C. with or without continuous mixing. The electrochemically active analyte complex must comprise at least the analyte to be tested and an electrochemically active label component. Formation of this complex at the surface of the sensor electrode is thus directly or indirectly proportional to the concentration of the analyte in the sample.

The analyte complex is formed at or on the electroconductive polymer layer of the sensor electrode, such that the electrochemically active label component is held in close physical proximity to the electroconductive polymer. The label component may thus have a direct or indirect effect on the redox properties of the electroconductive polymer and this effect provides an indication of the amount of analyte present in the sample, since formation of the complex comprising stoichiometric amounts of the analyte and the label component is directly or indirectly proportional to the concentration of the analyte in the sample. Thus, the conductive polymer coating is in effect the transducing element of the sensor, i.e the redox state of the conductive polymer acts as the transducer, converting the chemical signal associated with the concentration of the analyte into a measurable electrical signal.

The electrochemically active label component can be any label which directly or indirectly affects the redox properties of the electroconductive layer of the sensor electrode.

In a preferred embodiment the electrochemically active label component may be a charged label having the following properties:
a) it carries a net charge at the pH of the electrochemically active measuring solution; and
b) the magnitude of this charge changes when a pre-determined holding potential is induced at the sensor electrode, thereby charging the particle positively or negatively with respect to its preferred charge state.

Suitable charged labels are also characterised in that the magnitude of their charge changes in response to a change in the ionic strength of the measuring solution at constant pH, or in response to a change in pH at a constant ionic strength. This effect can be mimicked by inducing a pre-determined fixed potential at the sensor electrode, thereby charging the particle positively or negatively with respect to its preferred charge state. Thus in the method of the invention there is no need to carry out measurements of the potential of the sensor electrode versus a reference electrode in two separate measuring solutions—i.e. an inactive measuring buffer and a second buffer which differs from the measuring buffer with respect to pH at constant ionic strength or with respect to ionic strength at constant pH. Instead, the effect of transferring the label component from "inactive" to "active" buffer are mimicked by induction of the pre-determined potential. When the pre-determined potential is applied the magnitude of the charge on the charge label changes such that it has a detectable effect on the redox properties of the electroconductive polymer layer.

Preferred charged labels include, but are not limited to, gold, ferrocene or latex microspheres.

In a further preferred embodiment of the invention the electrochemically active label component may be an enzyme label. Suitable enzyme labels include any enzyme capable of converting a substrate into a product whereby the action of the enzyme directly or indirectly affects the redox composition of the electroconductive polymer coating of the sensor electrode.

In one embodiment the enzyme may be capable of converting a substrate which has no detectable effect on the redox composition of the electroconductive polymer coating of the sensor electrode to a product capable of directly or indirectly affecting the redox composition of the electroconductive polymer coating.

In a further embodiment the enzyme may be capable of converting a substrate capable of directly or indirectly affecting the redox composition of the electroconductive polymer coating of the sensor electrode to a product which has no detectable effect on the redox composition of the electroconductive polymer coating.

The enzyme product or substrate may directly or indirectly affecting the redox composition of the electroconductive polymer coating of the sensor electrode by virtue of a change in the chemical composition of the electroconductive polymer and/or by a change in pH and/or a change in ionic strength in the measuring solution proximal to the surface of the electroconductive polymer layer.

Preferred enzyme labels include, but are not limited to, horseradish peroxidase, alkaline phosphatase, urease, catalase and glucose oxidase.

In still further embodiments the label component may comprise, or form part of, a multi-subunit enzyme complex or a multi-enzyme cascade. For example, the enzyme label may be capable of converting a substrate which has no detectable effect on the redox composition of the electroconductive polymer coating of the sensor electrode to a product which is a substrate for a second enzyme, the action of the second enzyme generating a second product which directly or indirectly affects the redox composition of the electroconductive polymer coating of the sensor electrode. The second enzyme may also form part of the electrochemically active analyte complex, or may be separately associated with the electroconductive polymer layer of the sensor electrode. Alternatively, the first enzyme may be separately associated with the electroconductive polymer layer of the sensor electrode, or might even be present in the bulk solution, with the second enzyme forming part of the electrochemically active analyte complex.

Formation of the electrochemically active analyte complex can be performed in many ways as will be understood by those skilled in the art of diagnostic assay development, these include, inter alia, all forms of heterogeneous and homogeneous, competitive and sandwich assays, as described in further detail below.

The method of the invention may be adapted to perform quantitative assays for a wide range of analytes. In particular, the method may be used to perform electrochemical binding assays in sandwich or competitive formats.

A typical sandwich assay requires a "capture" receptor having specificity for the analyte of interest. The receptor may be essentially any type of specific binding agent capable of specifically binding to the analyte of interest. Suitable receptors include, but are not limited to, naturally occurring or recombinant biological binding agents such as, for example, antibodies or fragments thereof such as $F(ab')_2$ fragments, scAbs, Fv and scFv fragments etc., nucleic acids, lectins, all types of ligand-binding receptors, such as hormone receptors, cytokine receptors etc., nucleic acid binding proteins and aptamers.

The capture receptor is typically immobilised on the surface of the sensor electrode(s), for example it may be adsorbed to the surface of a polymer-coated electrode or incorporated into the polymer coating. When the sensor electrode is in use, any analyte present in the sample will bind to the immobilised capture receptor. Electrochemical detection of bound analyte requires a secondary receptor, capable of binding to the analyte at a site spatially distinct from the site of binding to the capture agent. The secondary receptor is typically conjugated with the label component, such as a charge or enzyme label, that permits electrochemical detection, as described herein. In this embodiment the "electrochemically active analyte complex" formed on the electroconductive polymer layer of the sensor electrode is a complex of capture receptor, analyte, secondary receptor and label component.

The affinity reaction steps of the above-described assay are equivalent to a standard sandwich binding assay well known to those skilled in the art. The sandwich format of analysis is particularly useful for the detection of polyvalent antigens, in which case the capture agent and labelled secondary receptor used in the test are preferably antibodies that bind to different, spatially distinct epitopes on the antigen. The sandwich format may also be used where the antigen carries two or more identical epitopes, which are spatially separated. In this latter embodiment, the capture agent and labelled secondary receptor used in the test may be antibodies of identical specificity.

A typical competitive binding assay also requires a "capture" receptor having specificity for the analyte of interest, which is typically immobilised on the surface of the sensor electrode(s), as described for the sandwich assay. When the sensor electrode is brought into contact with the sample, any analyte present in the sample will bind to the immobilised capture receptor. Competing molecules also capable of binding to the capture agent compete with the analyte for binding to the available capture agent. The competing molecules are labelled with a label component that enables electrochemical detection, e.g. a charge or enzyme label. In this embodiment the "electrochemically active analyte complex" formed on the electroconductive polymer layer of the sensor electrode is a complex of capture receptor, competing molecule and label component.

In the competitive electrochemical assay the competing molecules may be labelled analyte or labelled structural analogs of the analyte that are capable of binding to the same analyte binding site on the immobilized/adsorbed capture agent. The use of labelled analyte as the competing molecule is particularly preferred for the detection of small analyte molecules. Alternatively, the competing molecule may bind to a different site on the immobilized/adsorbed capture agent. For example, if the immobilized capture agent is an antibody, the competing molecule could be an anti-immunoglobulin antibody (preferably Fab-specific) or even an anti-idiotype antibody of the appropriate specificity. Competitive detection methods are usually dependent on there being an excess of capture sites on the surface of the sensor electrode. Those capture agents which do not bind analyte will be available for binding to the competing molecule. Assuming that the total number of capture binding sites remains constant, the amount of bound competing molecule will be inversely proportional to the amount of analyte present.

The affinity reaction steps of the above-described methods are substantially equivalent to standard sandwich or competitive enzyme linked immunosorbant assays (ELISA) well known to those skilled in the art. Although the method of the invention is particularly suitable for performing electrochemical ELISA assays it will be appreciated that the basic assay of the invention can be utilised to perform other types of assays involving changes in pH, ionic strength or redox potential, for example assays involving alternative receptors (e.g single stranded nucleic acids, enzymes, cell based systems etc). The method of the invention may also be used to perform direct enzymatic assays for analytes that are also substrates for a suitable enzyme. In such embodiments the enzyme, which also constitutes the label component, may be immobilised in or adsorbed directly on the eletroconductive polymer, rather than being conjugated to an additional receptor component.

After formation of the electrochemically active analyte complex the sensor electrode is brought into contact with an electrochemically active measuring solution or buffer which promotes electrochemical activity of the electrochemically active analyte complex. By "promotes electrochemical activity" is meant that the active measuring solution provides conditions which allow changes in a property or activity of the label component of the analyte complex, for example in response to application and subsequent removal of external current. This change in a property or activity of the label complex in turn directly or indirectly affects the redox properties of the electroconductive layer of the sensor electrode.

For example, in embodiments wherein the analyte complex includes a charged label component, the pH and/or ionic strength of the active measuring solution will be such that the magnitude of the charge on the charged label component may change in response to an externally applied current. The molarity, ionic strength and pH of active measuring solutions for use with charge labels may vary depending on the magnitude/strength and polarity of the charge on the lavel. In embodiments wherein the analyte complex includes an enzyme label component the active measuring solution may include a substrate for the enzyme. Suitable active measuring solutions for use with enzyme labels are low ionic strength buffers containing all reagents required for enzyme activation at the optimum pH for the particular enzyme, e.g. for horseradish peroxidase the buffer may be 50 mM citrate buffer (pH 5.0) containing 0.1 mg/ml OPD and 0.03% w/v hydrogen perborate.

Step (c) of contacting the sensor electrode with the electrochemically active measuring solution may be achieved in several different ways. In one embodiment the sensor electrode may be transferred from the solution comprising the sample of step (b) to the active measuring solution of part (c). The sensor electrode may be physically transferred from a first container or vessel holding the solution comprising the sample to a second, separate container or vessel holding the active measuring solution. The sensor electrode may be washed after removal from the solution comprising the sample to remove any traces of the sample solution, including removal of any unbound analyte, before transfer to the active measuring solution.

In a further embodiment of the method steps (b) and (c) may be performed in a single container or vessel, simply by adding an excess volume of the active measuring solution of part (c) to the solution comprising the sample of part (b), after the electrochemically active analyte complex has formed on the sensor surface. The excess addition of active measuring solution reduces any sample effect and at the same time removes lightly bound complexes. This embodiment works in the same way as embodiments wherein the sensor electrode is "transferred" to the measuring solution because the effect that is being measured occurs on the sensor surface and any reactions occurring in the bulk solution have little or no significant effect on the measurement of the complex bound at the surface of the conductive polymer coating.

In embodiments of the method which do not rely on the use of containers for the various solutions a drop of the solution comprising the sample may first be placed onto the sensor. When it is desired to replace the sample with active measuring solution the sensor may simply be washed to remove the sample solution and then a drop of the active measuring solution placed on the sensor.

The sensor is allowed to settle in the active measuring solution for a short period of time (typically from 10 sec to 60 sec) and then a current is applied to activate the sensor and move the sensor electrode potential to a pre-determined potential. The pre-determined potential preferably relates to what the resting potential of the sensor electrode versus a reference electrode would be in a control measuring solution of substantially similar composition to the active measuring solution but without the electrochemically active component. In the case of an enzyme label the control measuring solution would be a solution of identical composition, identical pH and identical ionic strength to the active measuring solution but lacking the enzyme substrate. In the case of a charged label the control measuring solution would be a solution of lower ionic strength or different pH to the active measuring buffer. For any give sensor system a suitable value, or narrow range of values, for the pre-determined potential can be simply determined by measuring the resting potential of the system in a control measuring solution as a calibration step. It will be appreciated that the chosen pre-determined potential can vary somewhat from the exact measured value of the resting potential without affecting the function of the assay method to a material extent. Once suitable values of pre-determined potential have been determined, or supplied, for a particular sensor system, it is not necessary to repeat this measurement each time the sensor is used.

Figure 1:
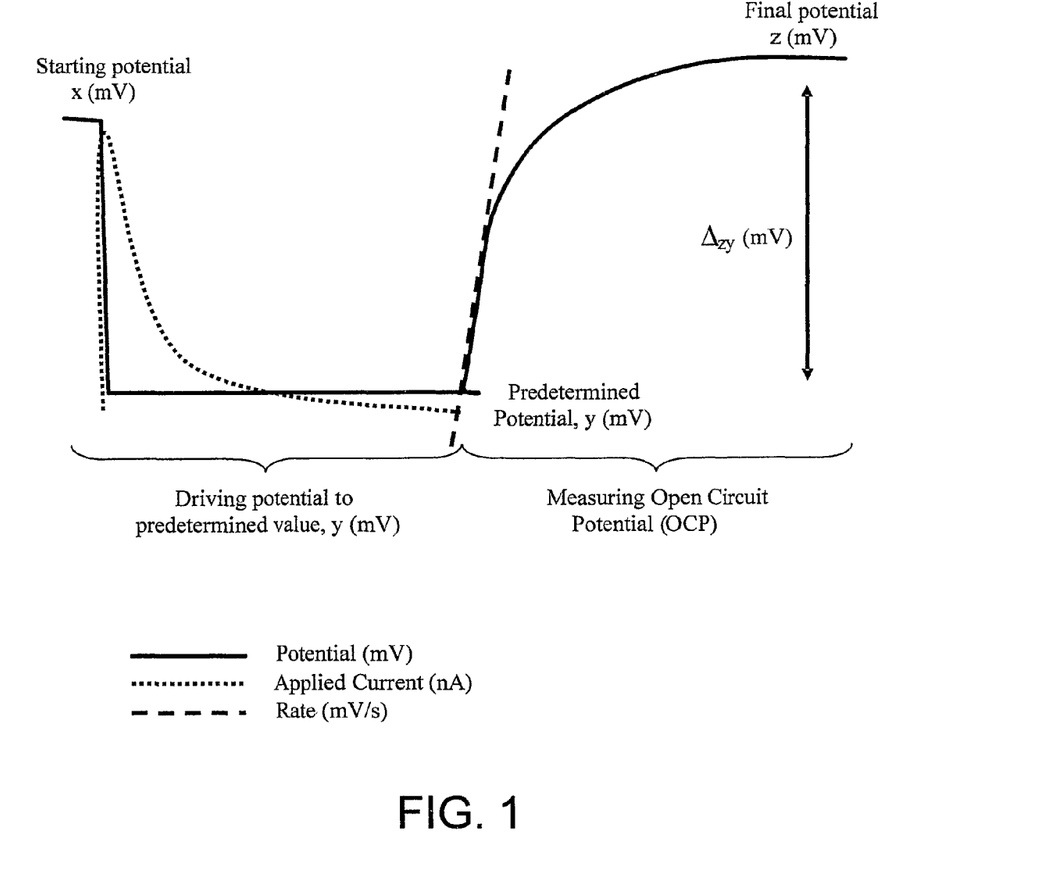
FIG. 1 is a schematic illustration of a method of measurement according to the invention where potential is driven to a predetermined potential, y, and then switched of and the open circuit potential is measured for a period of time (t) until a final potential, z, is achieved. $\Delta zy$ is measured, as is current and rate.

The current driving the pre-determined holding potential may be maintained to hold the sensor electrode at the pre-determined potential for a suitable period of time (typically 1 sec to 10 sec). The current is then switched off and the open circuit potential is measured for a defined time (typically 1 sec to 180 sec). During this period the potential of the sensor returns to its relaxed state due to the electrochemical activity of the analyte complex, FIG. 1(a). The time required for the sensor to return to its relaxed state depends on the reaction being measured and the concentration of that reaction occurring at the surface, this in turn being dependent on the amount of analyte present in the sample.

In the case of the analyte complexes incorporating enzyme labels an electrochemically active reaction (enzymatic conversion of substrate to product) is occurring continuously at the surface of the sensor electrode, thus the electrode quickly returns to an electrochemically induced resting potential once the holding current (electrically induced potential) has been removed. The difference between the electrically-induced holding potential and the electrochemically induced resting potential (also referred to herein as the open circuit resting potential) is indicative of the concentration of the analyte in the sample. (NB the value of this electrochemically induced resting potential in active measuring solution will be different from the resting potential in control buffer without the electrochemically active component)

In performing this method other measurements could be taken which would also be indicators of concentration of analyte, these are:

the amount of current required to hold a given pre-determined potential, and;
the initial rate at which the potential returns to the electrochemically induced resting potential.

Thus, the method of the invention may be based on measurement of any one of, or any combination of two or more of, the following parameters:

(i) the difference between the holding potential and the open circuit resting potential,
(ii) the rate at which the sensor electrode returns from the holding potential to the open circuit resting potential,
(iii) the amount of current required to hold the sensor electrode at the pre-determined holding potential.

It is most preferred for the method to be based on measurement of parameter (i), but inclusion of either or both of parameters (ii) and (iii) as "secondary measurements" would greatly improve reliance on the result of the analysis, because instead of just having one measurement three synergistically related measurements can be used. In addition, any one of these measurements could also be used to monitor the condition of the sensor electrode and signal whether it is defective in any way and therefore eliminate possible false results.

Figure 2:
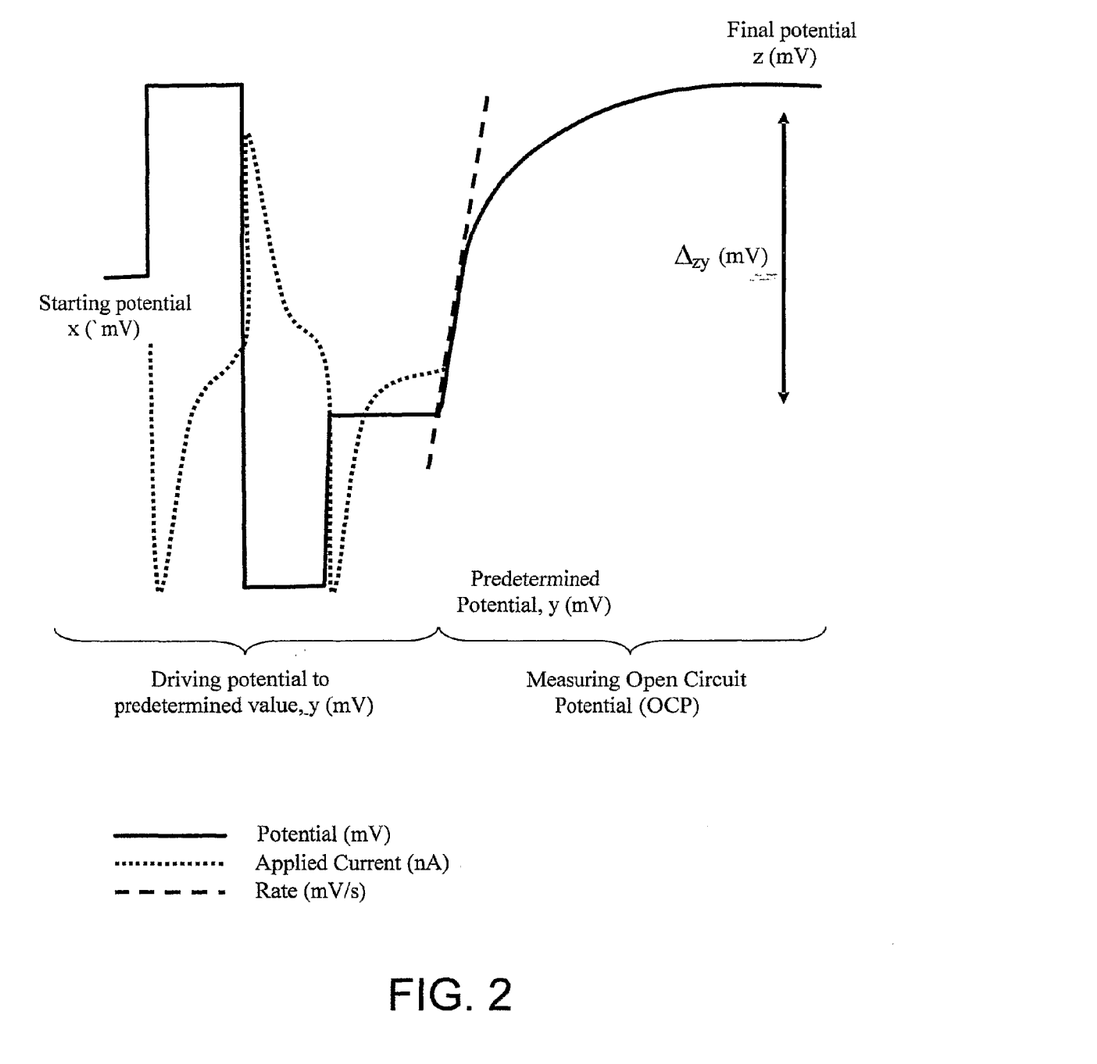
FIG. 2 is a schematic illustration of a method of measurement as for FIG. 1 but with a potential waveform prior to reaching a predetermined potential, y and the final measuring step.
Figure 3:
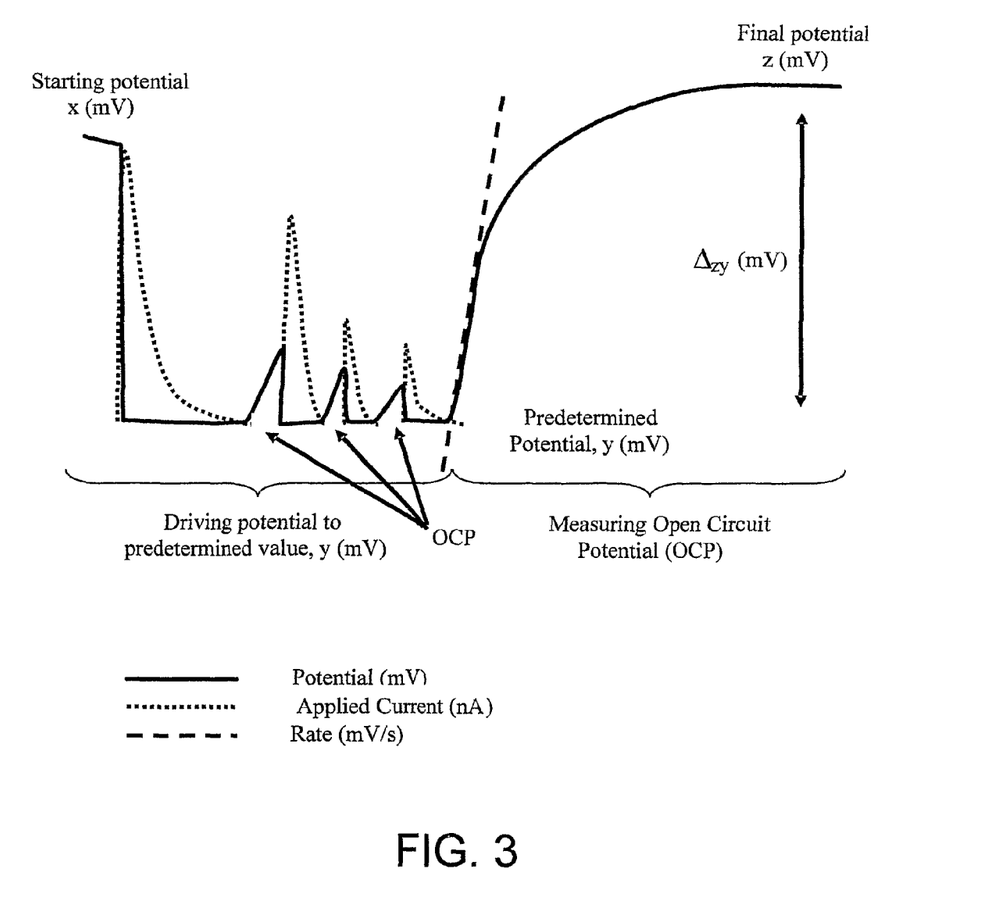
FIG. 3 is a schematic illustration of a method of measurement according to the invention which includes four driven potential and open potential cycles prior to final measurement step.

Although the method only requires the application of current to hold the sensor at a single pre-determined potential, alternative activation profiles may also be used to enhance the sensor response and to ensure the reference electrode is optimally equilibrated. For example, the sensor may be driven to more than one potential above or below the pre-determined potential before setting the potential prior to measuring the open circuit potential. Or several activation potentials and/or relaxation steps can be performed, as illustrated for example in FIGS. 2 and 3.

The measuring steps of the assay method of the invention, steps (d) to (f) require an electrode assembly comprising the sensor electrode, a reference electrode and a counter electrode or auxiliary electrode. The reference and counter electrode functions may be provided by a single electrode in a two-electrode system. Alternatively, separate counter and reference electrodes may be used in a three electrode system. Suitable reference electrodes include, for example, standard Ag/AgCl electrodes or calomel electrodes. Suitable counter electrodes include electrodes made of platinum, other noble metals or other inert conductive materials such as graphite or carbon.

The reference electrode and the counter electrode can be external to the sensor electrode or may be integrated with the sensor electrode to form an electrode assembly.

During the measuring steps, current is applied between the counter electrode and the sensor electrode in order to hold the sensor electrode at the pre-determined potential and the potential of the sensor electrode is measured relative to the reference electrode when all electrodes are in contact with the active measuring solution. Thus, the electrode assembly may be assembled after the formation of the electrochemically active analyte complex on the electroconductive polymer surface of the sensor electrode, but prior to or during contact with the active measuring solution. For example, the sensor, counter and reference electrodes may be fully or partially immersed in the active measuring solution and connected via suitable instruments to form an electrochemical cell. It is not necessary for the reference and counter electrodes to be brought into contact with the sample solution in step (b).

In further embodiments one or more sensor electrodes, counter electrodes and reference electrodes may be pre-formed in an integrated sensor assembly. The sensor assembly may be formed prior to coating of the sensor electrode with an electroconductive polymer layer, in which case the reference and counter electrodes can also be used for the purposes of electrochemical polymerisation of the polymer layer, as described in WO 00/11473 and WO 03/019171. Suitable sensor assemblies are also described in WO 00/11473 and WO 03/019171. Many different layouts of the final sensor assembly are possible including, for example, "dip-stick" type sensors, multiwell plates containing integrated electrochemical sensors (as described in WO 03/081253) and lateral flow devices incorporating electrochemical sensors (as described in WO 2004/010143).

The invention will be further understood with reference to the following non-limiting experimental example:

EXAMPLE 1

Unless otherwise stated all materials and reagents, and methods for their preparation, are as described in WO 00/11473 and WO 03/01-9171.

Prepare sensor electrodes coated with polypyrrole membrane with immobilised/adsorbed streptavidin using electrochemical coating techniques described in WO 00/11473 or WO 03/019171.

Wash streptavidin-coated sensors with 0.1M potassium phosphate buffer pH 7.8 by putting each sensor consecutively into three wells of a microtitre plate filled with 250 µl buffer (sensors can be stored in this buffer during the next step).

Prepare biotinylated horseradish peroxidase (HRP) concentrations in 0.1M potassium phosphate buffer pH 7.8. Regular concentrations used for QC are: 0.0, 0.05, 0.1, 0.2, 0.4, 0.6, 0.8 and 1.0 ng/ml. (Different concentrations may be required for other experiments)

Place 200 µl of each HRP-biotin concentration into a well of a microtitre plate.

Place one sensor per well. The working area of each sensor must be immersed completely in solution.

Incubate sensors with biotinylated-HRP concentrations at room temperature for 15 min.

Wash sensors with 0.1M potassium phosphate buffer pH 7.8. Note: after this step the sensors can be stored in washing buffer for 1-2 hours.

For measurement use a potentiostat (e.g. autolab) which can prime a sensor with a fixed potential and then measure open circuit potential.

Place the sensors in 50 mM citrate buffer pH 5.0 containing 0.1 mg/ml o-Phenylenediamine (OPD) and 0.03% w/v hydrogen perborate.

Figure 4:
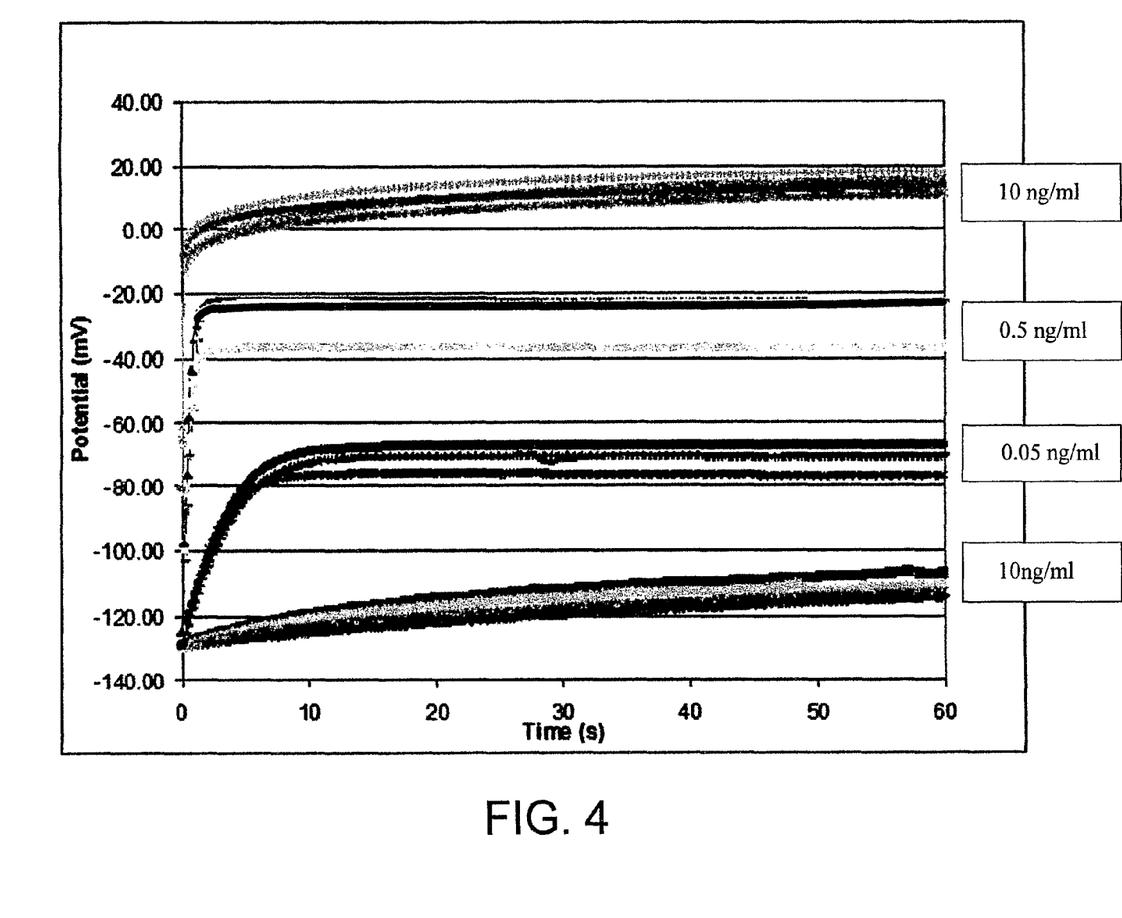
FIG. 4 shows the results of an assay using the method of the invention based on the use of horseradish peroxidase. Sensor electrode response (potential in mV) following exposure to various concentrations of HRP was measured after priming to a holding potential of −130 mV. Open circuit potential was measured for 60 s.

Prime the sensor at −130 mV for 10 sec and measure open circuit potential for 60 sec. Results are illustrated in FIG. 4.

The invention claimed is:
1. A method of electrochemical detection of an analyte in a sample consisting of:
(a) providing a sensor electrode comprising an electrically conductive electrode coated with a layer of electroconductive polymer;
(b) contacting the sensor electrode with a solution comprising the sample to be tested for the presence of the analyte under conditions which permit formation of an electrochemically active analyte complex comprising the analyte and an electrochemically active label component on the electroconductive polymer layer;
(c) contacting the sensor electrode plus electrochemically active analyte complex with an electrochemically active measuring solution which promotes electrochemical activity of the electrochemically active analyte complex;
(d) applying a current to induce a pre-determined holding potential on the sensor electrode;
(e) removing the current thereby allowing the sensor electrode to return to an open circuit resting potential; and
(f) measuring one or more of the following parameters as an indicator of the amount of analyte present in the sample:
(i) the difference between the pre-determined holding potential and the open circuit resting potential,

(ii) the initial rate at which the sensor electrode returns from the pre-determined holding potential to the open circuit resting potential; and (iii) the open circuit resting potential;

wherein optionally the sensor electrode plus electrochemically active anaylyte complex is washed prior to step (c).

2. The method according to claim 1 wherein in step (d) a constant current is applied such that the sensor electrode is held at a single pre-determined holding potential.

3. The method according to claim 1 wherein in step (d) the current is varied such that the sensor electrode is held at one or more different electrically induced potentials and/or open circuit potentials prior to the pre-determined holding potential.

4. The method according to claim 1, wherein step (c) is carried out by transferring the sensor electrode from the solution comprising the sample of step (b) to the measuring solution of step (c).

5. The method according to claim 1, wherein step (c) is carried out by adding an excess of the measuring solution of step (c) to the solution comprising the sample of step (b).

6. The method according to claim 1, wherein the electrochemically active label component of the electrochemically active analyte complex comprises an enzyme capable of converting a substrate to a product, the action of which directly affects the redox composition of the electroconductive polymer coating of the sensor electrode.

7. The method according to claim 6 wherein the enzyme is horseradish peroxidase, alkaline phosphatase, urease, catalase, or glucose oxidase.

8. The method according to claim 6 wherein the enzyme is capable of converting a substrate which has no detectable effect on the redox composition of the electroconductive polymer layer of the sensor electrode to a product which directly or indirectly affects the redox composition of the electroconductive polymer layer.

9. The method according to claim 6 wherein the enzyme is capable of converting a substrate which directly or indirectly affects the redox composition of the electroconductive polymer layer of the sensor electrode to a product which has no detectable effect on the redox composition of the electroconductive polymer layer.

10. The method according to claim 6 wherein the enzyme is capable of converting a substrate which has no detectable effect on the redox composition of the electroconductive polymer coating of the sensor electrode to a product which is a substrate for a second enzyme, the action of the second enzyme generating a second product the production of which directly or indirectly affects the redox composition of the electroconductive polymer coating of the sensor electrode.

11. The method according to claim 1, wherein the electrochemically active label component of the electrochemically active analyte complex comprises a charged label having the following properties:

a) it carries a net charge at the pH of the electrochemically active measuring solution of claim 1; and b) the magnitude of this charge changes when a predetermined holding potential is induced at the sensor electrode, thereby charging the particle positively or negatively with respect to its preferred charge state.

12. The method according to claim 11 wherein the charged label is gold, ferrocene or latex microspheres.

13. The method according to claim 1 wherein the electroconductive polymer layer of the sensor electrode has immobilized therein or adsorbed thereto capture receptors which are capable of binding quantitatively to the desired analyte to be detected in the sample.

14. The method according to claim 13 wherein formation of the electrochemically active analyte complex in step (b) is carried out by:

(b1) contacting the sensor electrode with a solution comprising the sample so that the analyte binds to the immobilized or adsorbed capture receptors;

(b2) contacting the sensor electrode with a solution comprising secondary receptors capable of binding to the analyte at a site spatially distinct from the site of binding to the capture receptors, said secondary receptors being conjugated with the label component.

15. The method according to claim 13 wherein formation of the electrochemically active analyte complex in step (b) is carried out by:

(b1) contacting the sensor electrode with a solution comprising the sample so that the analyte binds to the immobilized or adsorbed capture receptors;

(b2) contacting the sensor electrode with a solution comprising competing molecules capable of binding to the capture receptors, said competing molecules being conjugated with the label component.

16. The method according to claim 14 wherein steps (b1) and (b2) are performed simultaneously by contacting the sensor electrode with a solution comprising the sample to which has been added secondary receptors or competing molecules conjugated with the label component.

17. The method according to claim 1, wherein the sample is milk, a food homogenate or a soil extract.

18. The method according to claim 1, wherein the sample is a biological fluid.

19. The method according to claim 18 wherein the biological fluid is whole blood, serum, lymph, urine, saliva, ascites, pleural effusion, cerebrospinal fluid or semen.

* * * * *